United States Patent
Kawamoto et al.

(10) Patent No.: US 11,905,356 B2
(45) Date of Patent: *Feb. 20, 2024

(54) BISMALEIMIDE COMPOUND, COMPOSITION CONTAINING SAME, POLYBENZOXAZOLE, AND SEMICONDUCTOR DEVICE

(71) Applicant: Nippon Kayaku Kabushiki Kaisha, Tokyo (JP)

(72) Inventors: Naoki Kawamoto, Tokyo (JP); Firyon Ko, Tokyo (JP); Taihei Koumoto, Tokyo (JP)

(73) Assignee: Nippon Kayaku Kabushiki Kaisha, Tokyo (JP)

(*) Notice: Subject to any disclaimer, the term of this patent is extended or adjusted under 35 U.S.C. 154(b) by 24 days.

This patent is subject to a terminal disclaimer.

(21) Appl. No.: 17/685,604

(22) Filed: Mar. 3, 2022

(65) Prior Publication Data

US 2022/0298281 A1  Sep. 22, 2022

(30) Foreign Application Priority Data

Mar. 16, 2021 (JP) .................. 2021-042386
Feb. 15, 2022 (JP) .................. 2022-021273

(51) Int. Cl.
| | |
|---|---|
| C07D 207/24 | (2006.01) |
| C08F 222/40 | (2006.01) |
| C08L 79/08 | (2006.01) |
| C08J 5/18 | (2006.01) |
| C07D 207/22 | (2006.01) |
| H01L 23/532 | (2006.01) |
| H01L 23/29 | (2006.01) |
| H01L 21/027 | (2006.01) |
| C08F 122/40 | (2006.01) |
| C08F 22/40 | (2006.01) |
| C08F 236/14 | (2006.01) |

(52) U.S. Cl.
CPC ........ *C08F 222/408* (2020.02); *C07D 207/22* (2013.01); *C07D 207/24* (2013.01); *C08J 5/18* (2013.01); *C08L 79/085* (2013.01); *C08F 22/40* (2013.01); *C08F 122/40* (2013.01); *C08F 222/40* (2013.01); *C08F 222/404* (2020.02); *C08F 222/406* (2020.02); *C08F 236/14* (2013.01); *C08J 2379/08* (2013.01); *H01L 21/0271* (2013.01); *H01L 23/293* (2013.01); *H01L 23/5329* (2013.01)

(58) Field of Classification Search
CPC .............. C08F 222/40; C08F 222/404; C08F 222/406; C08F 236/14; C08F 22/40; C08F 122/40; C08L 79/085; C08J 2379/08; C07D 207/24; C07D 207/22
See application file for complete search history.

(56) References Cited

U.S. PATENT DOCUMENTS

| | | | |
|---|---|---|---|
| 4,371,685 A | 2/1983 | Ahne et al. | |
| 6,080,522 A | 6/2000 | Ito et al. | |
| 2010/0324163 A1* | 12/2010 | Shinjo ................. | C09D 11/101 522/43 |
| 2023/0250233 A1 | 8/2023 | Kawamoto et al. | |
| 2023/0305400 A1 | 9/2023 | Kawamoto et al. | |

FOREIGN PATENT DOCUMENTS

| | | |
|---|---|---|
| JP | 11-199557 A | 7/1990 |
| JP | 2-37934 B2 | 8/1990 |
| JP | 5-5995 A | 1/1993 |
| JP | 6-161102 A | 6/1994 |
| JP | 6-289626 A | 10/1994 |
| JP | 11-24271 A | 1/1999 |

* cited by examiner

*Primary Examiner* — Arrie L Reuther
*Assistant Examiner* — David L Miller
(74) *Attorney, Agent, or Firm* — NIELDS, LEMACK & FRAME, LLC

(57) ABSTRACT

An object of the present invention is to provide a novel photosensitive resin precursor that can be developed with an alkali and ring-closed even at low temperatures, and preferably has excellent thermal properties and excellent electric properties after curing, and also to provide a use application thereof. As means for achieving the object, disclosed are a bismaleimide compound comprising, in one molecule, two partial structures in each of which a carbon atom having a substituent represented by the following formula (A) (wherein Y represents a direct bond or a divalent linking group), and a carbon atom having a hydroxy group are directly bonded to each other, a polymer which is a self-polymer of the bismaleimide compound, and a benzoxazole which is an intramolecular dehydrated ring-closed product of the polymer.

[Chemical Formula 1]

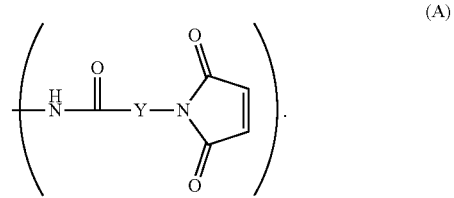

(A)

6 Claims, No Drawings

BISMALEIMIDE COMPOUND, COMPOSITION CONTAINING SAME, POLYBENZOXAZOLE, AND SEMICONDUCTOR DEVICE

CROSS REFERENCE TO RELATED APPLICATIONS

This application claims priority to Japanese Patent Application No. 2021-042386 filed with the Japan Patent Office on Mar. 16, 2021, which is incorporated herein by reference in its entirety.

BACKGROUND OF THE INVENTION

Technical Field

The present invention relates to a bismaleimide compound, a composition using the bismaleimide compound, a polybenzoxazole, and a semiconductor element. The bismaleimide compound of the present invention can be applied to a protective film, an interlayer insulating film, an insulating film of a rewiring layer, and the like for a semiconductor element.

Background Art

Conventionally, a polyimide resin, a polybenzoxazole resin, and the like, which are excellent in heat resistance, mechanical properties, and others, have been widely used for a surface protective film of a semiconductor element, an interlayer insulating film thereof, etc. (see Patent Literature 1: JP-A-11-199557). When a polyimide resin or a polybenzoxazole resin is used as a surface protective film or an interlayer insulating film, a method for forming a through hole or the like by an etching method using a positive photoresist containing these resins has been known. However, this method has had a problem that complicated steps such as application of a photoresist and peeling thereof are required. Therefore, for the purpose of streamlining a work process, a heat-resistant material to which photosensitivity is imparted has been studied (see Patent Literature 2: JP-A-11-24271).

A thin film of a polyimide resin or a polybenzoxazole resin having excellent heat resistance and excellent mechanical properties can be generally obtained by thermally dehydrating and ring-closing a coating film of a precursor of the polyimide resin or the polybenzoxazole resin, and at that time, firing at a high temperature of about 350° C. is usually required. However, for example, a next-generation memory such as a magnetoresistive random access memory (MRAM) or resins used for sealing the memory are weak against high temperatures. Therefore, it is required for a polyimide resin or a polybenzoxazole resin used for an interlayer insulating film of a fan-out wafer level package that forms a rewiring structure on a surface protective film of such an element or a sealing resin thereof to be cured by firing at a low temperature of about 300° C. or lower and to obtain various properties comparable to those of a conventional material fired at a high temperature of about 350° C.

In addition, a polyimide resin that has been conventionally used needs to use a large amount of an organic solvent such as N-methyl-2-pyrrolidone in a development step thereof, and the cost is high. Therefore, due to not only necessity of cost reduction but also safety and the recent increase in concerns to environmental issues, there is a demand for non-use of an organic solvent. On the other hand, there have been proposed methods using various heat-resistant resin materials that can be developed (patterned) with a dilute alkali aqueous solution like photoresist, such as a method for mixing a polyamic acid with a compound having an amino group, an amide group, a urethane group, or the like, and heating the mixture after exposure to light in the presence of a photoinitiator (see Patent Literature 3: JP-A-06-289626), a method for mixing a quinone diazide with a salt of a polyamic acid and an amine compound having a phenolic hydroxy group (see Patent Literature 4: JP-A-06-161102), and a method for mixing a polyamic acid with a base generator such as nifedipine (see Patent Literature 5: JP-A-05-5995).

Each of these methods uses a positive photosensitive composition based on polyamic acid. Such a photosensitive composition exhibits relatively good developability, but has a small difference in solubility between an exposed portion and an unexposed portion, and therefore has a large pattern film loss and insufficient photosensitivity. In addition, since the composition has a large amount of free carboxylic acid in a polymer backbone chain thereof, the backbone chain is hydrolyzed over time by acidity of the polymer itself, and storage stability is extremely low disadvantageously.

Patent Literature 6 (JP-B-02-37934) proposes a negative photosensitive material in which a hydroxy group derived from an epoxy ring generated when a photosensitive group is introduced via an ester bond by allowing a glycidyl methacrylate to act on a carboxy group of a polyamic acid is blocked with an intramolecular cyclic acid anhydride. However, since the photosensitive material disclosed in the literature also has a large amount of free carboxylic acid in a polymer thereof, the photosensitive material has various problems. For example, there is a concern that storage stability is low due to an influence of hydrolysis of the backbone chain and photosensitive side chain over time, and in addition, in such a photosensitive material, an imidization reaction proceeds by heating at the time of introducing a photosensitive group, and a target polymer cannot be obtained.

Furthermore, data communication amount of communication terminals typified by smartphones is continuously increasing, and a communication frequency is made to be higher in order to transmit a large amount of data in a short time. In order to make the communication frequency higher, it is necessary to suppress a transmission loss, and materials having a low dielectric constant and a low dielectric loss tangent are required. However, it has been difficult to achieve both the properties as described above and the dielectric properties.

CITATION LIST

Patent Literature

Patent Literature 1: JP-A-11-199557
Patent Literature 2: JP-A-11-24271
Patent Literature 3: JP-A-06-289626
Patent Literature 4: JP-A-06-161102
Patent Literature 5: JP-A-05-5995
Patent Literature 6: JP-B-02-37934

SUMMARY OF THE INVENTION

Technical Problem

An object of the present invention is to provide a novel bismaleimide compound.

Another object of the present invention is to provide a composition containing the novel compound, a polybenzoxazole, and a semiconductor element.

Still another object of the present invention is to provide a compound which has excellent developability and from which a cured film (preferably a cured film having excellent thermal properties and excellent electrical properties) can be obtained even by heat treatment at a low temperature of 300° C. or lower (or light irradiation and heat treatment at 300° C. or lower).

Solution to Problem

As a result of intensive studies, the present inventors have found that by using a polybenzoxazole which is a dehydrated ring-closed product of a polymer of a bismaleimide compound (heat-resistant resin) having a specific structure, a cured film can be obtained even by heat treatment a low temperature of 300° C. or lower (or light irradiation and heat treatment at 300° C. or lower).

That is, various aspects of the present invention are as follows.

[1].

A bismaleimide compound comprising, in one molecule, two partial structures in each of which a carbon atom having a substituent represented by the following formula (A):

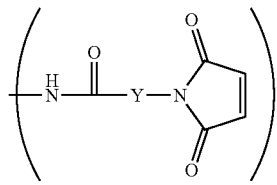

(A)

(wherein Y represents a direct bond or a divalent linking group), and a carbon atom having a hydroxy group are directly bonded to each other.

[2].

The bismaleimide compound according to [1], represented by the following formula (1)

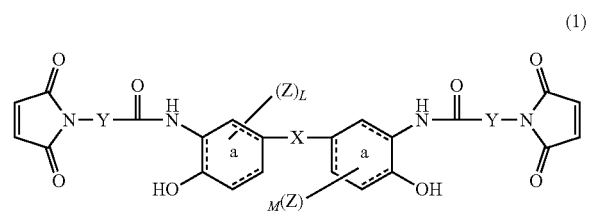

(1)

(wherein ring a represents a benzene ring or a cyclohexane ring, X and Y each independently represent a direct bond or a divalent linking group, the plurality of Ys may be the same as or different from each other, Z represents a monovalent substituent bonded to ring a, when there is a plurality of Zs, Zs may be the same as or different from each other, and L and M each represent the number of substituents Zs and each independently represent an integer of 0 to 3.)

[3].

The bismaleimide compound according to [2], wherein X represents a direct bond or a divalent linking group containing one or more selected from the group consisting of a carbon atom, a fluorine atom, a sulfur atom, and an oxygen atom.

[4].

The bismaleimide compound according to [3], wherein X represents a direct bond or a divalent linking group represented by any one of the following formulas (a) to (f):

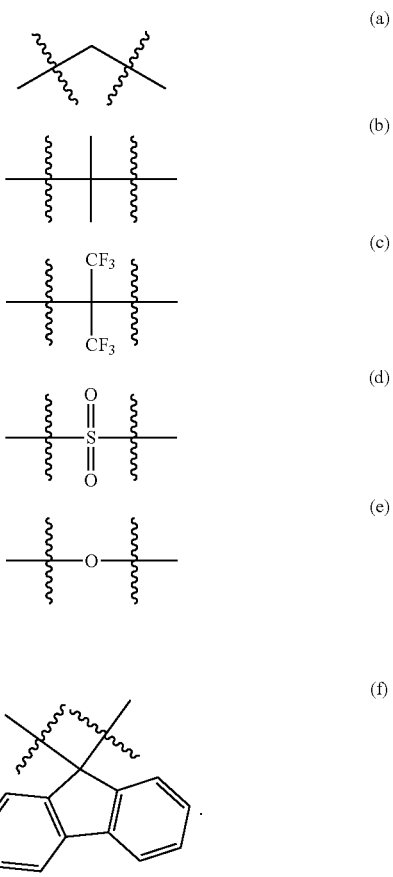

[5].

The bismaleimide compound according to any one of [1] to [4], wherein Y represents an alkylene group having 1 to 11 carbon atoms or an alkylene group having 1 to 11 carbon atoms and including a divalent aromatic group.

[6].

A composition comprising the bismaleimide compound according to any one of [1] to [5] and a compound capable of reacting with a maleimide group.

[7].

A composition comprising the bismaleimide compound according to any one of [1] to [5] and a photopolymerization initiator or a curing catalyst.

[8].

A polymer comprising 2 to 150 structural units each represented by the following formula (2):

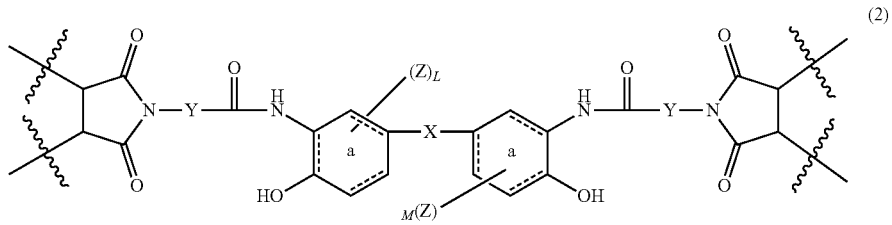

(wherein X, Y, Z, L, M, and ring a have the same meanings as X, Y, Z, L, M, and ring a in formula (1) in [1]), which is a self-polymer of the bismaleimide compound according to any one of [2] to [5] or a copolymer of the composition according to [6].

[9].

A polybenzoxazole comprising 2 to 150 structural units each represented by the following formula (3):

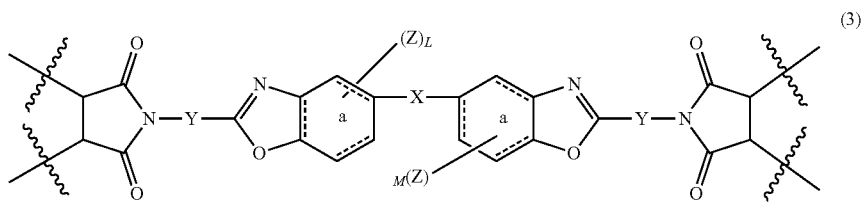

(wherein X, Y, Z, L, M, and ring a have the same meanings as X, Y, Z, L, M, and ring a in formula (1) in [1]), which is an intramolecular dehydrated ring-closed product of the polymer according to [8].

[10].

A semiconductor element comprising a surface protective film, an interlayer insulating film, or an insulating film of a rewiring layer each containing the polybenzoxazole according to [9].

[11].

A dry film resist obtained by sandwiching a composition containing the bismaleimide compound according to any one of [1] to [5] and a photopolymerization initiator between substrates.

A composition containing the compound or the like of the present invention can be developed with an alkaline aqueous solution, and by using the composition, a cured film can be obtained even by heat treatment at a low temperature of 300° C. or lower (or light irradiation and heat treatment at 300° C. or lower). In addition, the cured film according to a preferred embodiment of the present invention has excellent thermal properties and electrical properties.

DESCRIPTION OF THE EMBODIMENTS

Hereinafter, embodiments of the present invention will be described in detail, but the present invention is not limited thereto.

A bismaleimide compound of the present invention has (hereinafter, also simply sometimes referred to as "compound of the present invention"), in one molecule, two partial structures in each of which a carbon atom having a substituent represented by the following formula (A) and a carbon atom having a hydroxy group are directly bonded to each other.

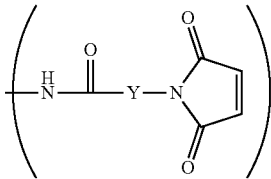

In formula (A), Y represents a direct bond or a divalent linking group.

The divalent linking group represented by Y in formula (A) is not particularly limited, but is preferably an alkylene group having 1 to 11 carbon atoms or an alkylene group having 1 to 11 carbon atoms and including a divalent aromatic group. Note that the divalent alkylene group referred to herein is not limited to a linear alkylene group, and may be a branched or cyclic divalent alkylene group.

The divalent linking group represented by Y in formula (A) is more preferably an alkylene group having 1 to 11 carbon atoms, still more preferably an alkylene group having 2 to 8 carbon atoms, particularly preferably an alkylene group having 5 carbon atoms or an alkylene group represented by the following formula (g), and most preferably an alkylene group represented by the following formula (g), from the viewpoints of film physical properties and solubility.

The direct bond represented by Y in formula (A) is a structure in which a nitrogen atom in a maleimide ring and a carbon atom in a carbonyl group specified in formula (A)

are directly bonded to each other by a single bond without any atom or the like interposed therebetween.

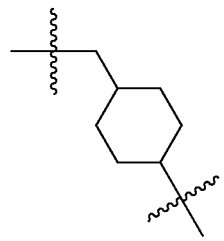
(g)

The direct bond between a carbon atom having the substituent represented by formula (A) and a carbon atom having a hydroxy group may be any of a single bond, a double bond, and a carbon-carbon bond with resonance in an aromatic compound or the like.

The partial structure in which a carbon atom having the substituent represented by formula (A) and a carbon atom having a hydroxy group are directly bonded to each other by a single bond is a tetravalent linking group represented by the following formula (B), and the partial structure in which a carbon atom having the substituent represented by formula (A) and a carbon atom having a hydroxy group are directly bonded to each other by a double bond is a divalent linking group represented by the following formula (C). The partial structure in which a carbon atom having the substituent represented by formula (A) and a carbon atom having a hydroxy group are directly bonded to each other by a carbon-carbon bond with resonance is exemplified by the following formula (D). Note that Ar in formula (D) represents an aromatic ring.

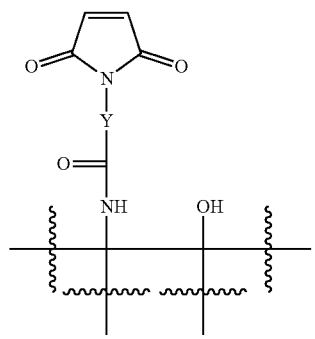
(B)

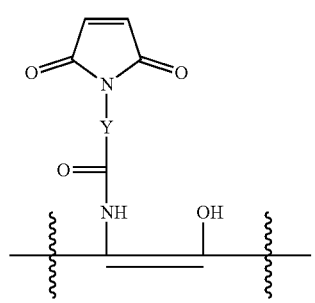
(C)

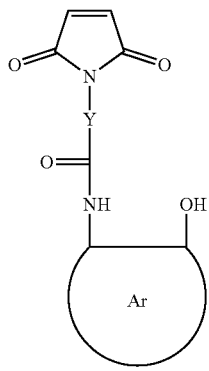
(D)

The direct bond between a carbon atom having the substituent represented by formula (A) and a carbon atom having a hydroxy group is preferably a single bond or a carbon-carbon bond with resonance in an aromatic compound or the like. More preferably, two adjacent carbon atoms on a cyclo ring have the substituent represented by formula (A) and a hydroxy group, respectively, or two adjacent carbon atoms on an aromatic ring have the substituent represented by formula (A) and a hydroxy group, respectively. Still more preferably, two adjacent carbon atoms on a cyclohexane ring have the substituent represented by formula (A) and a hydroxy group, respectively, or adjacent carbon atoms on a benzene ring have the substituent represented by formula (A) and a hydroxy group, respectively. That is, examples of the preferred compound of the present invention include a compound represented by the following formula (1).

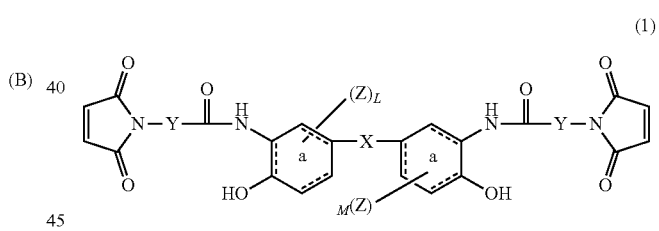
(1)

In formula (1), ring a represents a benzene ring or a cyclohexane ring. That is, the bismaleimide compound represented by formula (1) is a compound having a structure in which two benzene rings are bonded to each other by a direct bond or a divalent linking group, or a structure in which two cyclohexane rings are bonded to each other by a direct bond or a divalent linking group, as a backbone.

In formula (1), X and Y each independently represent a direct bond or a divalent linking group, and the plurality of Ys may be the same as or different from each other.

The divalent linking group represented by X in formula (1) is not particularly limited, but examples thereof include an element belonging to group 16, such as an oxygen atom, a methylene group (methanediyl group), an ethane-1,2-diyl group, an ethane-2,2-diyl group, a propane-2,2-diyl group (isopropylidene group), a propane-1,3-diyl group, a propane-2,3-diyl group, a trifluoromethylmethanediyl group, a di(trifluoromethyl) methanediyl group (hexafluoroisopropylidene group), a sulfonyl group, and a fluorenyl group.

The divalent linking group represented by X in formula (1) is preferably an oxygen atom, a methylene group (methanediyl group), an ethane-1,2-diyl group, an ethane-2,2-diyl group, a propane-2,2-diyl group, a propane-1,3-diyl group, a propane-2,3-diyl group, a trifluoromethylmethanediyl group, a di(trifluoromethyl) methanediyl group, a sulfonyl group, or a fluorenyl group, from the viewpoint of film physical properties and solubility. The divalent linking group represented by X in formula (1) is more preferably an oxygen atom, a propane-2,2-diyl group, a di(trifluoromethyl) methanediyl group, or a sulfonyl group, and still more preferably a di(trifluoromethyl) methanediyl group or a sulfonyl group.

X in formula (1) is preferably a direct bond or a divalent linking group containing one or more selected from the group consisting of a carbon atom, a fluorine atom, a sulfur atom, and an oxygen atom. The "divalent linking group containing one or more selected from the group consisting of a carbon atom, a fluorine atom, a sulfur atom, and an oxygen atom" as used herein is not particularly limited as long as it is a divalent linking group containing one or more of these atoms, but is more preferably a divalent linking group represented by any of the following formulas (a) to (f).

That is, X in formula (1) is more preferably a direct bond or a divalent linking group represented by any one of the following formulas (a) to (f).

Note that the direct bond represented by X in formula (1) is a structure in which two rings a specified in formula (1) are directly bonded to each other by a single bond without any atom or the like interposed therebetween.

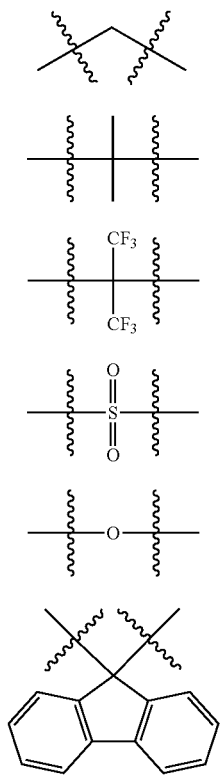

Examples of the divalent linking group represented by Y in formula (1) include a divalent linking group represented by Y in formula (A). Preferred examples of the divalent linking group represented by Y in formula (1) are also the same as the above-mentioned preferable examples of the divalent linking group represented by Y in formula (A).

In formula (1), Z represents a monovalent substituent of a benzene ring or a cyclohexane ring which is ring a. That is, among six carbon atoms on the benzene ring or cyclohexane ring which is ring a, each of three carbon atoms which are not replaced with the substituent represented by formula (A), a hydroxy group, or X has a substituent Z or is bonded to a hydrogen atom.

The monovalent substituent represented by Z is not particularly limited, but is preferably a halogen atom, a hydroxy group, a nitro group, a cyano group, an aliphatic group, an aromatic group, an acetyl group, a carboxyl group, an ester group, an amide group, a trifluoromethyl group, an imide group, or a urea group. When there is a plurality of Zs, the Zs may be the same as or different from each other. L and M each represent the number of substituents Zs, each independently represent an integer of 0 to 3, and each independently preferably represent an integer of 0 or 1.

Specific examples of the halogen atom which is a preferred aspect of Z in formula (1) include a fluorine atom, a bromine atom, a chlorine atom, and an iodine atom. Among these atoms, a fluorine atom is preferable.

The aliphatic group which is a preferred aspect of Z in formula (1) is a residue obtained by removing one hydrogen atom from a hydrocarbon compound having no aromaticity. The hydrocarbon compound is not limited to any of a linear form, a branched form, and a cyclic form, and may be a compound having a plurality of these forms.

Specific examples of the aliphatic group which is a preferred aspect of Z in formula (1) include an alkyl group having 1 to 6 carbon atoms, such as a methyl group, an ethyl group, a propyl group, or a cyclohexane group, an alkenyl group having 1 to 6 carbon atoms, such as propenyl group, and an alkynyl group having 1 to 6 carbon atoms, such as propynyl group. Among these groups, a methyl group is preferable.

The aromatic group which is a preferred aspect of Z in formula (1) is a residue obtained by removing one hydrogen atom from an aromatic ring of an aromatic compound. The aromatic compound is not limited to any of an aromatic hydrocarbon compound, a heterocyclic compound, a heterocyclic condensed aromatic compound, and the like as long as it is a compound having aromaticity.

Specific examples of the aromatic group which is a preferred aspect of Z in formula (1) include a phenyl group and a naphthyl group. Among these groups, a phenyl group is preferable.

Specific examples of the ester group which is a preferred aspect of Z in formula (1) include a methoxycarbonyl group, an ethoxycarbonyl group, a n-proxycarbonyl group, a benzyloxycarbonyl group, and a phenoxycarbonyl group. Among these groups, a phenoxycarbonyl group is preferable.

Specific examples of the amide group which is a preferred aspect of Z in formula (1) include an alkylamide group such as —$CONH_2$, —$CONH(CH_3)$, or —$CONH(i\text{-}C_3H_7)$, and an arylamide group such as benzamide, naphthamide, p-t-butylbenzamide, o-chlorobenzamide, or —$CON(Ph)_2$. Among these groups, benzamide is preferable. Note that in the present specification, Ph represents a phenyl group.

Z in formula (1) is more preferably an aliphatic group from the viewpoint of ease of dehydration ring-closing at low temperatures.

A method for manufacturing the compound of the present invention is not particularly limited, but in general, a method for converting a maleimide carboxylic acid into a halide derivative using a halogenating agent, and then reacting the halide derivative with a diaminodiphenol compound or a cyclohexane ring compound obtained by hydrogenating a benzene ring of the diaminodiphenol compound (hereinafter, referred to as a diaminodiphenol compound or a hydrogenated product thereof) is used. In the reaction between the halide derivative and the diaminodiphenol compound or a hydrogenated product thereof, it is preferable to use the halide derivative in an amount of 2 times to slightly larger than 2 times by mole with respect to the diaminodiphenol compound or a hydrogenated product thereof.

The halide derivative is preferably a chloride derivative. Examples of the halogenating agent used in the conversion of the maleimide carboxylic acid into the chloride derivative include thionyl chloride, oxalyl chloride, phosphoryl chloride, and phosphorus chloride which have been used in a usual acid chlorination reaction.

The maleimide carboxylic acid may be synthesized from a corresponding amino acid by a known method, or a commercially available product may be used.

Examples of the maleimide carboxylic acid used for manufacturing the compound of the present invention include, but are not limited to, the following compounds of Nos. 1 to 4. These maleimide carboxylic acids can be used singly or in combination of two or more types thereof.

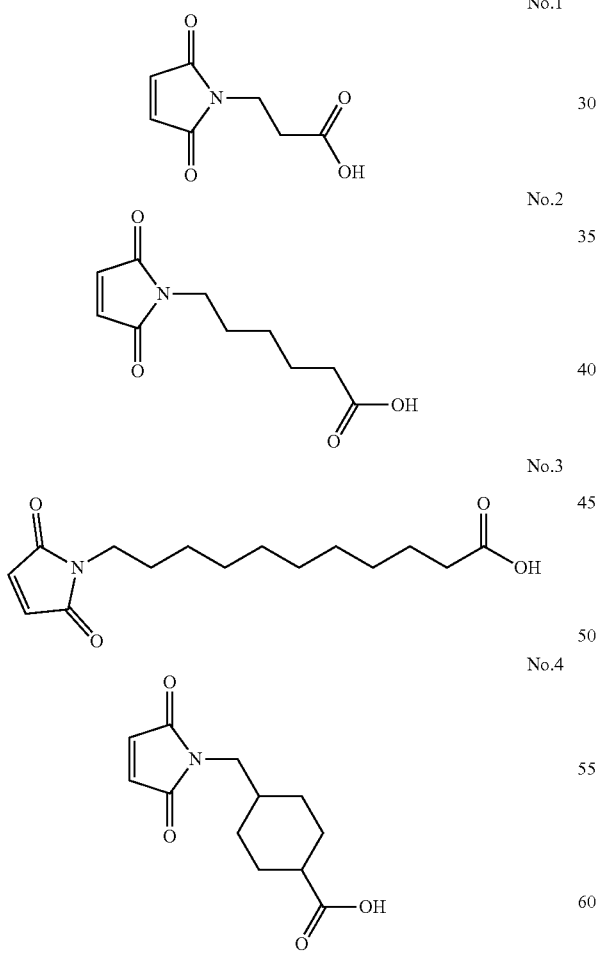

Examples of the diaminodiphenol compound or a hydrogenated product thereof used for manufacturing the compound of the present invention include, but are not limited to, the following compounds of Nos. 5 to 12 and cyclohexane ring compounds obtained by hydrogenating benzene rings in the compounds of Nos. 5 to 12.

These diaminodiphenol compounds or hydrogenated products thereof can be used singly or in combination of two or more types thereof.

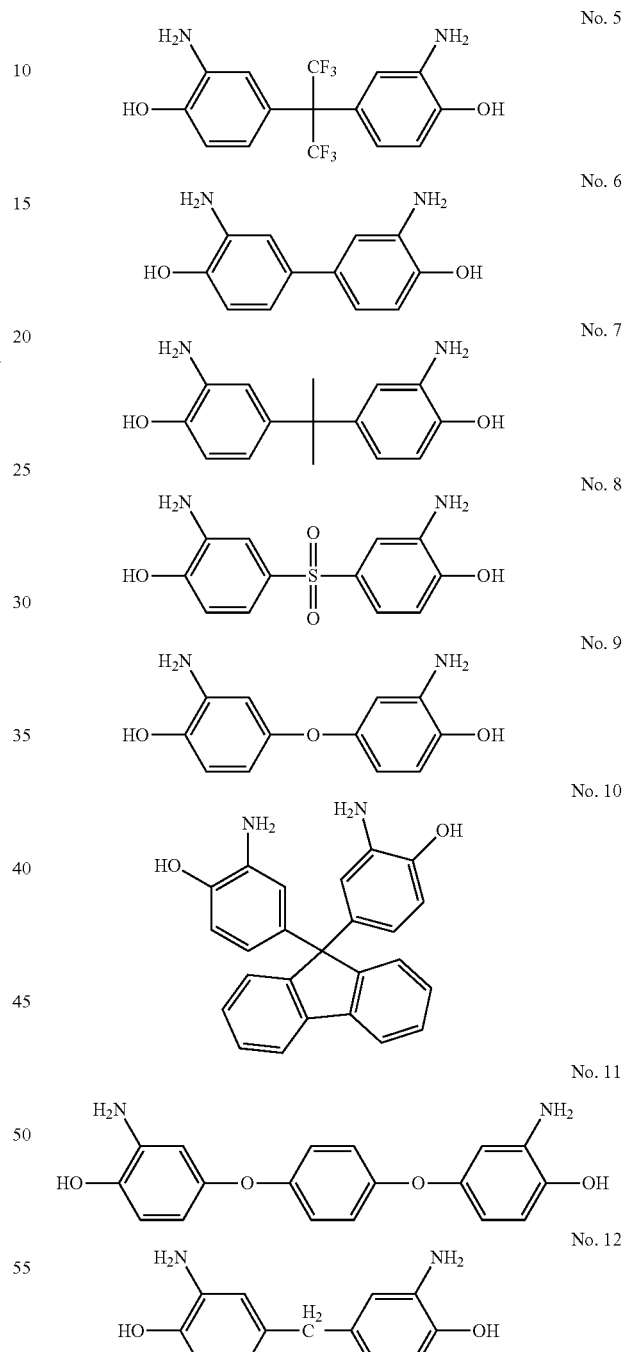

The reaction between the halide derivative and the diaminodiphenol compound or a hydrogenated product thereof is desirably performed in an organic solvent in the presence of a dehalogenating agent. As the dehalogenating agent, usually, an organic base such as pyridine, picoline, or triethylamine can be used. As the organic solvent, sulfolane, N,N-dimethylacetamide, N-methyl-2-pyrrolidone, N,N-dimethylformamide, or the like can be used. The concentration of these reaction components with respect to the entire reaction system including a solvent is not particularly limited, but is preferably 20 to 80% by mass, and more preferably 40 to 60% by mass.

As a specific synthesis procedure, first, a maleimide carboxylic acid is dissolved in an organic solvent, and a halide derivative is synthesized using a halogenating agent. Subsequently, a diaminodiphenol compound or a hydrogenated product thereof is added thereto in the presence of a dehalogenating agent. A temperature at which the diaminodiphenol compound or a hydrogenated product thereof is added is preferably −20 to 25° C., and more preferably 0 to 20° C. A reaction temperature of the halide derivative and the diaminodiphenol compound or a hydrogenated product thereof is preferably 0 to 80° C., and more preferably 50 to 70° C. Reaction time is preferably 30 minutes to 24 hours, and more preferably one to eight hours. After completion of the reaction, water can be added to the obtained reaction solution to obtain the desired compound.

By subjecting the compound obtained by the above procedure to a treatment with an acidic aqueous solution, an alkaline aqueous solution, or a neutral aqueous solution, and optionally an organic solvent, and the like, impurities can be removed.

Next, a polymer of the present invention will be described.

The compound of the present invention represented by formula (1) can be formed into the polymer of the present invention having a structural unit represented by the following formula (2), which is a polymer (self-polymer) obtained by self-polymerization of the compound represented by formula (1) through maleimide groups at both terminals, or a polymer (copolymer) obtained by copolymerization of the compound represented by formula (1) and a compound capable of reacting with a maleimide group. That is, the self-polymer has a structure in which a plurality of the unit structures represented by the following formula (2) are directly bonded to each other. The copolymer has a structure in which a plurality of the unit structures represented by the following formula (2) are bonded to each other via a linking group other than formula (2). The number of unit structures represented by formula (2) in the polymer of the present invention is not particularly limited, but is preferably 2 to 150.

Note that X, Y, Z, L, M, and ring a in the unit structure represented by formula (2) have the same meanings as X, Y, Z, L, M, and ring a in formula (1), and preferred ones in formula (2) are also the same as preferred ones in formula (1).

are reacted with each other. Under relatively mild heating conditions such as heating at 50 to 70° C. for about 60 to 180 minutes, a mixture of the compound represented by formula (1) and the self-polymer, containing the compound represented by formula (1) as a main component, is obtained, and under relatively severe heating conditions such as heating at 80° C. to 120° C. for 30 to 120 minutes, a mixture of the compound represented by formula (1) and the self-polymer, containing the self-polymer as a main component, is obtained. Since a ratio between the compound represented by formula (1) and the self-polymer in the mixture affects handling and the like when the mixture is subjected to a subsequent step, the ratio therebetween (reaction conditions) only needs to be selected in consideration of handling and the like.

Note that even a mixture containing the compound represented by formula (1) as a main component also undergoes a self-polymerization reaction by being heated during a ring closing reaction for benzimidazolation. Therefore, such a compositional ratio of the mixture hardly has an undesirable influence on physical properties of a finally obtained polybenzimidazole.

The compound represented by formula (1) can be self-polymerized alone, but can also be self-polymerized after being formed into a composition by using a photopolymerization initiator or a curing catalyst in combination with the compound represented by formula (1). By using the photopolymerization initiator in combination, the compound represented by formula (1) can be self-polymerized by light irradiation. In addition, by using the curing catalyst in combination, a heating temperature at the time of self-polymerization can be lowered than that at the time of not using the curing catalyst.

The photopolymerization initiator that can be used in combination at the time of self-polymerization is not particularly limited, and those conventionally used can be appropriately employed. Specific examples of the photopolymerization initiator include acetophenone, 2,2-dimethoxyacetophenone, p-dimethylaminoacetophenone, Michler's ketone, benzyl, benzoin, benzoin methyl ether, benzoin ethyl ether, benzoin isopropyl ether, benzoin n-propyl ether, benzoin isopropyl ether, benzoin n-butyl ether, benzyl dimethyl ketal, thioxanthone, 2-chlorothioxanthone, 2-methylthioxanthone, 2,2-dimethoxy-1,2-diphenylethan-1-one, 1-hydroxy-cyclohexyl-phenyl-ketone, 2-hydroxy-2-methyl-1-phenyl-propan-1-one, 1-[4-(2-hydroxyethoxy)-phenyl]-2-hydroxy-2-methyl-1-propan-1-one, 2-hydroxy-1-{4-[4-(2-hydroxy-2-methyl-propionyl)-benzyl] phenyl}-2-methyl-propan-1-one, 2-methyl-1-[4-(methylthio) phenyl]-2-morpholinopropan-1-one, 2-benzyl-2-dimethylamino-1-(4-

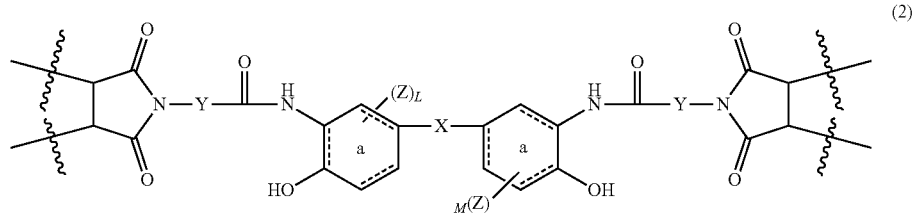

(2)

The compound represented by formula (1) can be self-polymerized only by being heated at usually 40 to 150° C. for about 30 to 300 minutes. Conditions for the self-polymerization are not particularly limited as long as they are conditions usually performed when maleimide groups morpholinophenyl)-1-butanone, 2,4,6-trimethylbenzoyl-diphenyl-phosphine oxide, bis(2,4,6-trimethylbenzoyl)-phenylphosphine oxide, 1-[4-(phenylthio) phenyl]-1,2-octanedione=2-O-benzyloxime), 1-[9-ethyl-6-(2-methylbenzoyl)-9H-carbazol-3-yl] ethanone 1-(O- acetyloxime), and 2,4-diethylthioxanthone. These photopolymerization initiators may be used singly or in combination of two or more types thereof.

Among these photopolymerization initiators, it is preferable to use a photopolymerization initiator that can efficiently generate radicals at an exposure wavelength of 310 to 436 nm (more preferably 365 nm) from the viewpoint that a fine pattern can be formed using a reduction projection exposure machine (stepper; light source wavelength: 365 nm or 436 nm) typically used in a process of manufacturing a semiconductor protective film or the like. Preferable examples of the photopolymerization initiator include 1-[4-(phenylthio) phenyl]-1,2-octanedione=2-(O-benzoyloxime) ("IRGACURE OXE-01" manufactured by BASF Japan Ltd.), 1-[9-ethyl-6-(2-methylbenzoyl)-9H-carbazol-3-yl] ethanone 1-(O-acetyloxime) ("IRGACURE OXE-02" manufactured by BASF Japan Ltd.), 2,4-diethylthioxanthone ("DETX-S" manufactured by Nippon Kayaku Co., Ltd.), and 2-methyl-1-[4-(methylthio) phenyl]-2 morpholinopropan-1-one ("Omirad 907" manufactured by IGM Resins B.V.).

The amount of the photopolymerization initiator is preferably 0.1 to 20 parts by mass, and more preferably 1 to 5 parts by mass with respect to 100 parts by mass of the compound represented by formula (1) (in a case where the photopolymerization initiator is used).

A sensitizer may be used in combination with the photopolymerization initiator. The sensitizer that can be used in combination is not particularly limited as long as it is a conventionally known sensitizer, but examples thereof include 4,4'-bis(diethylamino) benzophenone.

The amount of the sensitizer is preferably 2 parts by mass or less, and more preferably 0.05 to 0.5 parts by mass with respect to 100 parts by mass of the compound represented by formula (1) (in a case where the sensitizer is used). By using the sensitizer in combination, the sensitivity to light during self-polymerization can be enhanced.

The curing catalyst that can be used in combination in the self-polymerization is not particularly limited as long as it can promote the self-polymerization of the maleimide groups at both terminals of the compound of the present invention represented by formula (1) by heating, and those conventionally used can be appropriately employed. Specific examples of the curing catalyst include: an imidazole such as 2-methylimidazole, 2-ethylimidazole, 2-phenylimidazole, 2-ethyl-4 methylimidazole, 2-undecylimidazole, or 1-cyanoethyl-2-ethyl-4-methylimidazole; an amine such as triethylamine, triethylenediamine, 2-(dimethylaminomethyl) phenol, 1,8-diaza-bicyclo (5,4,0) undecene-7, tris (dimethylaminomethyl) phenol, or benzyldimethylamine; a phosphine such as triphenylphosphine, tributylphosphine, or trioctylphosphine; an organic metal salt such as tin octylate, zinc octylate, dibutyltin dimaleate, zinc naphthenate, cobalt naphthenate, or tin oleate; a metal chloride such as zinc chloride, aluminum chloride, or tin chloride; an organic peroxide such as di-tert-butyl peroxide or dicumyl peroxide; an azo compound such as azobisisobutyronitrile or azobisdimethylvaleronitrile; a mineral acid such as hydrochloric acid, sulfuric acid, or phosphoric acid; a Lewis acid such as boron trifluoride; and a salt such as sodium carbonate or lithium chloride.

The amount of the curing catalyst is preferably 10 parts by mass or less, and more preferably 1 to 5 parts by mass with respect to 100 parts by mass of the compound represented by formula (1) (in a case where the curing catalyst is used).

Examples of the compound that can react with a maleimide group used for copolymerization with the compound represented by formula (1) include a compound having a plurality of unsaturated double bonds such as an acrylic group, a methacrylic group, an allyl group, and a styryl group. It is a preferable aspect to perform copolymerization by light irradiation using these compounds in combination because the sensitivity to light can be enhanced, and a polyfunctional acrylate is more preferable from the viewpoint that a crosslinking reaction by photopolymerization can easily proceed.

Specific examples of the compound having a plurality of acrylic groups include hydrogenated dicyclopentadienyl diacrylate, dicyclopentenyl acrylate, dicyclopentenyloxyethyl acrylate, 1,3-butanediol diacrylate, 1,4-butanediol diacrylate, 1,6-hexanediol diacrylate, diethylene glycol diacrylate, neopentyl glycol diacrylate, polyethylene glycol 200 diacrylate, polyethylene glycol 400 diacrylate, polyethylene glycol 600 diacrylate, diethylene glycol diacrylate, neopentyl glycol diacrylate, hydroxypivalate neopentyl glycol diacrylate, triethylene glycol diacrylate, bis(acryloxyethoxy) bisphenol A, bis(acryloxyethoxy) tetrabromobisphenol A, tripropylene glycol diacrylate, trimethylolpropane triacrylate, pentaerythritol triacrylate, pentaerythritol tetraacrylate, dipentaerythritol hexaacrylate, and dipentaerythritol monohydroxypentaacrylate.

Specific examples of the compound having a plurality of methacrylic groups include a compound in which an acrylic group in the above-described compound having a plurality of acrylic groups is replaced with a methacrylic group.

Specific examples of the compound having a plurality of allyl groups include diallyl adipate, diallyl fumarate, diallyl hexahydrophthalate, pentaerythritol tetraallyl ether, glycerol diallyl ether, and triallyl citrate.

Specific examples of the compound having a plurality of styryl groups include bis(vinylphenyl) methane, bis(vinylphenyl) ethane, and bis(vinylphenyl) hexane.

A ratio between the compound represented by formula (1) and the compound capable of reacting with a maleimide group, used in the copolymerization, is not particularly limited, but can be appropriately adjusted depending on the molecular weight of the compound capable of reacting with a maleimide group, the number of polymerizable functional groups, and the like. For example, the amount of the compound capable of reacting with a maleimide group is preferably 0.01 to 10 mol, and more preferably 0.1 to 1 mol with respect to 1 mol of the compound represented by formula (1).

Note that the copolymerization only needs to be performed under the above-described various conditions of the self-polymerization, or may be performed using a photopolymerization initiator, a sensitizer, or a curing catalyst in combination. These usages are the same as those described in the section of the self-polymerization.

The polybenzoxazole of the present invention is an intramolecular dehydrated ring-closed product of the above-described polymer (self-polymer and copolymer) of the present invention, and has a unit structure represented by the following formula (3).

Note that X, Y, Z, L, M, and ring a in the unit structure represented by formula (3) have the same meanings as X, Y, Z, L, M, and ring a in formula (1), and preferred ones in formula (3) are also the same as preferred ones in formula (1).

In the entire specification and attached claims, the intramolecular dehydrated ring-closed product of the polymer having the unit structure represented by formula (3), including not only a case where ring a is a benzene ring but also a case where ring a is a cyclohexane ring formed by hydrogenation of a benzene ring, is collectively referred to as "polybenzoxazole" for convenience.

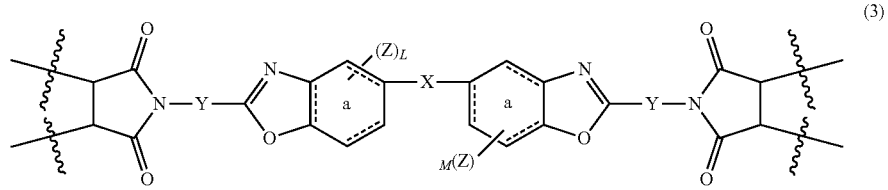

(3)

Conditions for dehydrating and ring-closing the polymer of the present invention are not particularly limited as long as they are conditions usually used when a benzoxazole precursor is formed into a benzoxazole by a dehydration ring-closing reaction. The dehydration ring-closing reaction can be performed by using, for example, a hot plate, an oven, or a temperature rising type oven in which a temperature program can be set. As an atmospheric gas at the time of thermal conversion, air may be used, and an inert gas such as nitrogen or argon can also be used.

The dehydration ring-closing reaction of the polymer of the present invention can be advantageously performed at a low temperature of 300° C. or lower. The temperature of the dehydration ring-closing reaction may be preferably lower than 300° C., and more preferably 290° C. or lower.

The composition of the present invention can contain a bismaleimide compound having, in one molecule, two partial structures in each of which a carbon atom having a substituent represented by formula (A) and a carbon atom having a hydroxy group are directly bonded to each other, or a component other than the bismaleimide compound represented by formula (1). Examples of another component that can be contained in the composition of the present invention include an organic solvent, a photopolymerization initiator, a thermoplastic resin, a colorant, a thickener, a thermal polymerization inhibitor, an antifoaming agent, a leveling agent, a curing agent or a curing catalyst having a reactive group capable of reacting with a maleimide group, and an adhesion enhancer such as a coupling agent. Various components other than the above components can also be used without particular limitation according to an application and a usage of the composition. A composition containing an organic solvent is preferable from the viewpoint of easy handling.

In addition, the compound of the present invention can undergo a self-polymerization reaction, and therefore can be used without using a photopolymerization initiator, a curing agent, a curing catalyst, or the like.

The curing agent is not particularly limited, and a conventionally used compound can be appropriately employed. The curing agent is not particularly limited as long as it is a compound having a functional group (or structure) capable of undergoing a crosslinking reaction with a maleimide group, such as an amino group, a cyanate group, a phenolic hydroxy group, or an alcoholic hydroxy group. In addition, a bismaleimide compound other than the bismaleimide compound of the present invention may be used in combination.

The organic solvent is not particularly limited, but examples thereof include γ-butyrolactone, ethyl lactate, propylene glycol monomethyl ether acetate, benzyl acetate, n-butyl acetate, ethoxyethyl propionate, 3-methyl methoxypropionate, N-methyl-2-pyrrolidone, N-ethyl-2-pyrrolidone, N,N-dimethylformamide, N,N-dimethylacetamide, dimethyl sulfoxide, hexamethylphosphorylamide, tetramethylene sulfone, cyclohexanone, cyclopentanone, diethyl ketone, diisobutyl ketone, and methyl amyl ketone. These organic solvents can be used singly or in combination of two or more types thereof. Use of an organic solvent in combination is a preferable aspect in that handling of the composition is improved.

The content of the organic solvent in the composition of the present invention is not particularly limited, but is usually 95% by mass or less, and preferably 20 to 90% by mass with respect to the total weight of the composition.

The coupling agent is not particularly limited, but may be typically a silane coupling agent. The silane coupling agent is not particularly limited, but examples thereof include 3-chloropropyltrimethoxysilane, vinyltrichlorosilane, vinyltriethoxysilane, vinyltrimethoxysilane, vinyl tris(2-methoxyethoxy) silane, 3-methacryloxypropyltrimethoxysilane, 2-(3,4-epoxycyclohexyl) ethyltrimethoxysilane, 3-glycidoxypropyltrimethoxysilane, 3-mercaptopropyltrimethoxysilane, 3-aminopropyltriethoxysilane, N-2-(aminoethyl)-3-aminopropyltrimethoxysilane, and 3-ureidopropyltriethoxysilane. These silane coupling agents can be used singly or in combination of two or more types thereof.

Since the silane coupling agent is unreactive with the compound or the like (compound, self-polymer, or polybenzoxazole) of the present invention, the silane coupling agent excluding a component that acts at the interface with a substrate may be present as a residual component after curing. Therefore, when such an adhesion enhancer is used in a large amount, it may have an undesirable influence such as degradation of physical properties. Since even a small amount of the silane coupling agent exhibits an effect depending on the type of the substrate, it is appropriate to use the silane coupling agent within a range in which the silane coupling agent does not have an undesirable influence. The amount of the silane coupling agent is usually 15% by mass or less, and preferably more than 0% by mass and 5% by mass or less with respect to the total weight of the composition, but an upper limit of the amount may vary depending on the type of the substrate.

Examples of the thermoplastic resin include polyethersulfone, polystyrene, and polycarbonate.

Examples of the colorant include phthalocyanine blue, phthalocyanine green, iodine green, crystal violet, titanium oxide, carbon black, and naphthalene black.

Examples of the thickener include orbene, bentone, and montmorillonite.

Examples of the thermal polymerization inhibitor include hydroquinone and 2,6-di-tert-butyl-p-methylphenol.

Examples of the antifoaming agent include silicone-based, fluorine-based, and polymer-based antifoaming agents.

The amount of each of these additives is, for example, preferably 30% by mass or less in the composition of the present invention (when these additives are used) as a rough indication, but may be appropriately increased or decreased according to a purpose of use.

In the composition of the present invention, for example, an inorganic filler such as barium sulfate, barium titanate, silicon oxide, amorphous silica, talc, clay, magnesium carbonate, calcium carbonate, aluminum oxide, aluminum hydroxide, or mica powder may be used in combination. The amount of the inorganic filler (if it is used) is preferably 60% by mass or less in the composition of the present invention.

A heat-resistant resin cured film formed of the polybenzoxazole of the present invention can be used for an electronic component such as a semiconductor device or a multilayer wiring board, or an organic EL display device. Specifically, this cured film can be suitably used for applications such as a passivation film of a semiconductor, a surface protective film of a semiconductor element, an interlayer insulating film thereof, an interlayer insulating film of high-density mounting multilayer wiring, an insulating film of a rewiring layer, an interlayer insulating film of an electronic component such as an inductor or an SAW filter, and an insulating film of an organic electroluminescent element or a flat layer thereof, but can have various structures without being limited thereto.

The compound and composition of the present invention can also be used in a form of a dry film resist. That is, the compound and the composition of the present invention can be formed into a dry film resist by applying the compound and the composition onto a base film using a roll coater, a die coater, a knife coater, a bar coater, a gravure coater, or the like, then drying the compound and the composition in a drying furnace set at 45 to 140° C. to remove a predetermined amount of solvent, and laminating a cover film or the like thereon as necessary. At this time, the thickness of the resist on the base film can be controlled to 2 to 200 μm. As the base film and the cover film, for example, a film of polyester, polypropylene, polyethylene, TAC, or polyimide is used. As these films, a film treated with a silicone-based release treatment agent or a non-silicone-based release treatment agent may be used as necessary. When the composition of the present invention is supplied as a dry film resist, the steps of applying the composition onto a support and drying the composition can be omitted, and the composition of the present invention can be used more easily.

EXAMPLES

Hereinafter, the present invention will be described more specifically with reference to specific examples, but the present invention is not limited to them. Note that "part" and "%" in Examples are on a mass basis.

Example 1

Synthesis of Compound (Compound A-1) Represented by General Formula (1)

In a 500 ml round bottom flask equipped with a stirring bar coated with Teflon®, 6.76 parts (0.040 mol) of 3-maleimidopropionic acid (compound of No. 1 above) and 20 parts of DMF were charged. The mixture was cooled with ice. Thereafter, 10.15 parts (0.080 mol) of oxalyl chloride was slowly added thereto, and the mixture was stirred at room temperature for two hours. Subsequently, a solution obtained by dissolving 7.33 parts (0.020 mol) of 4,4'-(hexafluoroisopropylidene) bis(2-aminophenol) (compound of No. 5 above) in 10 parts of DMF was added thereto, and the mixture was stirred at 60° C. for three hours. The mixture was cooled to room temperature, and then 300 parts of water was added thereto, and a precipitated solid was collected by filtration. The solid obtained above was dissolved in 30 parts of cyclopentanone. Thereafter, the solution was washed with 10 parts of dilute hydrochloric acid and then with 10 parts of water to obtain an organic layer from which unreacted raw materials had been removed. The organic layer was concentrated under vacuum to obtain 5.3 parts of a compound A-1 solution (solid content: 40%) (yield: 16%).

A-1

Example 2

Synthesis of Compound (Compound A-2) Represented by General Formula (1)

In a 500 ml round bottom flask equipped with a stirring bar coated with Teflon®, 8.44 parts (0.040 mol) of 6-maleimidohexanoic acid (compound of No. 2 above) and 20 parts of DMF were charged. The mixture was cooled with ice. Thereafter, 10.15 parts (0.080 mol) of oxalyl chloride was slowly added thereto, and the mixture was stirred at room temperature for two hours. Subsequently, a solution obtained by dissolving 7.33 parts (0.020 mol) of 4,4'-(hexafluoroisopropylidene) bis(2-aminophenol) (compound of No. 5 above) in 10 parts of DMF was added thereto, and the mixture was stirred at 60° C. for three hours. The mixture was cooled to room temperature, and then 300 parts of water was added thereto, and a precipitated solid was collected by filtration. The solid obtained above and 100 parts of methanol were put in a flask, and stirred and washed at 40° C.

Thereafter, cyclopentanone was added thereto, and the mixture was concentrated under vacuum to obtain 22.5 parts of a compound A-2 solution (solid content: 68%) (yield: 47%).

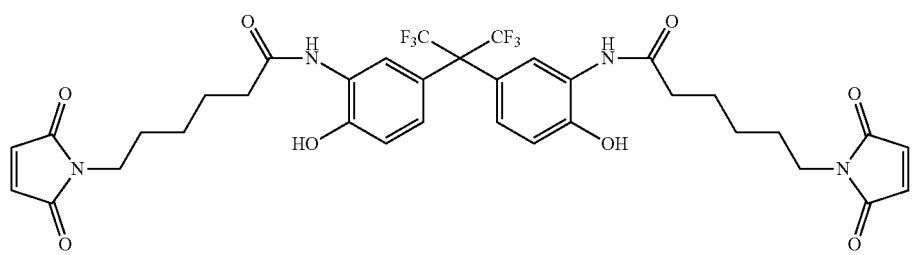

A-2

Example 3

Synthesis of Compound (Compound A-3) Represented by General Formula (1)

In a 500 ml round bottom flask equipped with a stirring bar coated with Teflon®, 9.50 parts (0.040 mol) of 4-(N-maleimidomethyl) cyclohexane-1-carboxylic acid (compound of No. 4 above) and 20 parts of DMF were charged. The mixture was cooled with ice. Thereafter, 10.15 parts (0.080 mol) of oxalyl chloride was slowly added thereto, and the mixture was stirred at room temperature for two hours. Subsequently, a solution obtained by dissolving 7.33 parts (0.020 mol) of 4,4'-(hexafluoroisopropylidene) bis(2-aminophenol) (compound of No. 5 above) in 10 parts of DMF was added thereto, and the mixture was stirred at 60° C. for three hours. The mixture was cooled to room temperature, and then 300 parts of water was added thereto, and a precipitated solid was collected by filtration. The solid obtained above was dissolved in 180 parts of cyclopentanone. Thereafter, the solution was washed with 60 parts of dilute hydrochloric acid three times and with 60 parts of sodium bicarbonate water once to obtain an organic layer from which unreacted raw materials had been removed. The organic layer was concentrated under vacuum to obtain 31 parts of a compound A-3 solution (solid content: 40%) (yield: 77%).

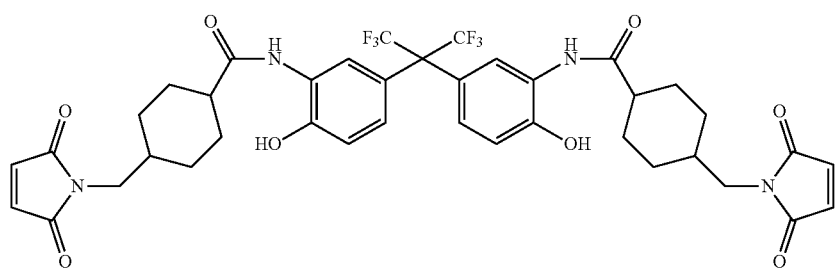

A-3

Example 4

Synthesis of Compound (Compound A-4) Represented by General Formula (1)

In a 500 ml round bottom flask equipped with a stirring bar coated with Teflon®, 8.44 parts (0.040 mol) of 6-maleimidohexanoic acid (compound of No. 2 above) and 20 parts of DMF were charged. The mixture was cooled with ice. Thereafter, 10.15 parts (0.080 mol) of oxalyl chloride was slowly added thereto, and the mixture was stirred at room temperature for two hours. Subsequently, a solution obtained by dissolving 4.33 parts (0.020 mol) of 3,3'-diamino-4,4'-dihydroxybiphenyl (compound of No. 6 above) in 10 parts of DMF was added thereto, and the mixture was stirred at 60° C. for three hours. The mixture was cooled to room temperature, and then 300 parts of water was added thereto, and a precipitated solid was collected by filtration. The solid obtained above and 100 parts of methanol were put in a flask, and stirred and washed at 40° C. Thereafter, a solid from which unreacted raw materials had been removed was collected by filtration, thereby obtaining 9.6 parts of compound A-4 (yield 80%).

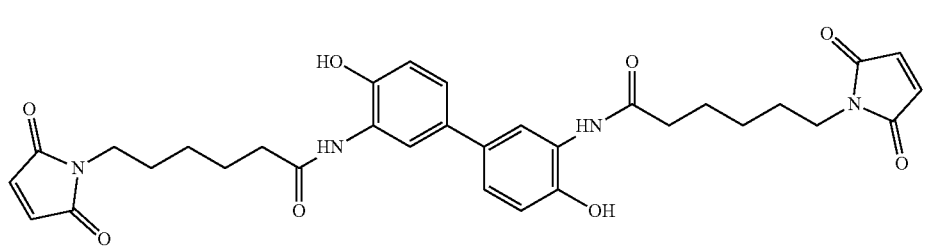

A-4

Example 5

Synthesis of Compound (Compound A-5) Represented by General Formula (1)

In a 500 ml round bottom flask equipped with a stirring bar coated with Teflon®, 9.49 parts (0.040 mol) of 4-(N-maleimidomethyl) cyclohexane-1-carboxylic acid (compound of No. 4 above) and 20 parts of DMF were charged. The mixture was cooled with ice. Thereafter, 10.15 parts (0.080 mol) of oxalyl chloride was slowly added thereto, and the mixture was stirred at room temperature for two hours. Subsequently, a solution obtained by dissolving 4.33 parts (0.020 mol) of 3,3'-diamino-4,4'-dihydroxybiphenyl (compound of No. 6 above) in 10 parts of DMF was added thereto, and the mixture was stirred at 60° C. for three hours. The mixture was cooled to room temperature, and then 300 parts of water was added thereto, and a precipitated solid was collected by filtration. The solid obtained above and 100 parts of methanol were put in a flask, and stirred at 40° C. Thereafter, a solid was collected by filtration to remove unreacted raw materials, thereby obtaining 4.0 parts of compound A-5 (yield 30%).

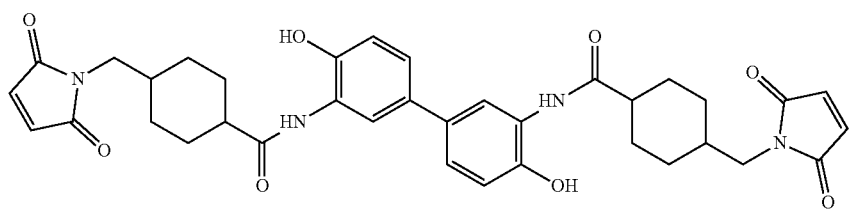

A-5

Example 6

Synthesis of compound (compound A-6) represented by general formula (1)

In a 500 ml round bottom flask equipped with a stirring bar coated with Teflon®, 19.3905 g (0.0918 mol) of 6-maleimidohexanoic acid (compound of No. 2 above) and 44.6085 g of NMP were charged. The mixture was cooled with ice. Thereafter, 12.5655 g (0.1056 mol) of thionyl chloride was slowly added thereto, and the mixture was stirred at 5° C. or lower for 30 minutes. Thereafter, a solution obtained by dissolving 7.9046 g (0.0306 mol) of 2,2-bis(3-amino-4-hydroxyphenyl) propane (compound of No. 7 above), 0.019 g of BHT, 10.4572 g of NMP, and 7.1202 g of picoline was added thereto, and the mixture was stirred for 50 minutes. After 50 minutes, the whole amount of the solution was slowly added dropwise to 1000 g of water to obtain a solid of a target product. The solid was dissolved in 80 g of acetone, and the whole amount of the solution was slowly added dropwise to 1000 g of water to cause reprecipitation. The solid was dried under vacuum and collected. The amount of the obtained solid (compound A-6) was 16.77 g, and an yield thereof was 85%.

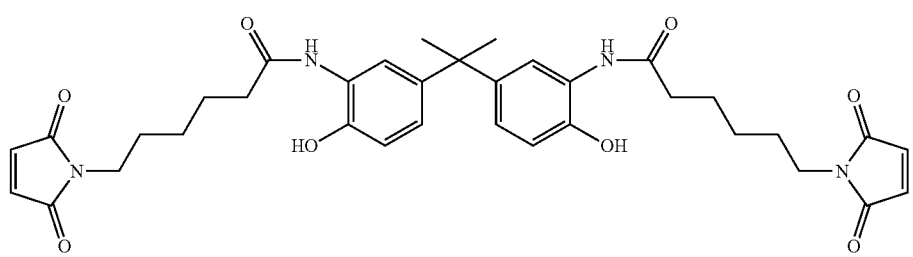

A-6

Example 7

Synthesis of Compound (Compound A-7) Represented by General Formula (1)

In a 500 ml round bottom flask equipped with a stirring bar coated with Teflon®, 18.9922 g (0.0800 mol) of 4-(N-maleimidomethyl) cyclohexane-1-carboxylic acid (compound of No. 4 above) and 83.72 g of NMP were charged. The mixture was cooled with ice. Thereafter, 20.40 g (0.1600 mol) of thionyl chloride was slowly added thereto, and the mixture was stirred at 5° C. or lower for 30 minutes. Thereafter, a solution obtained by dissolving 12.2114 g (0.040 mol) of bis(3-amino-4-hydroxyphenyl) sulfone (compound of No. 8 above), 0.019 g of BHT, 12.9168 g of NMP, and 10.13 g of picoline was added thereto, and the mixture was stirred for 50 minutes. After 50 minutes, the whole amount of the solution was slowly added dropwise to 1000 g of water to obtain a solid of a target product. The solid was dissolved in 80 g of acetone, and the whole amount of the solution was slowly added dropwise to 1000 g of water to cause reprecipitation. The solid was dried under vacuum and collected. The amount of the obtained solid (compound A-7) was 15.00 g, and an yield thereof was 52%.

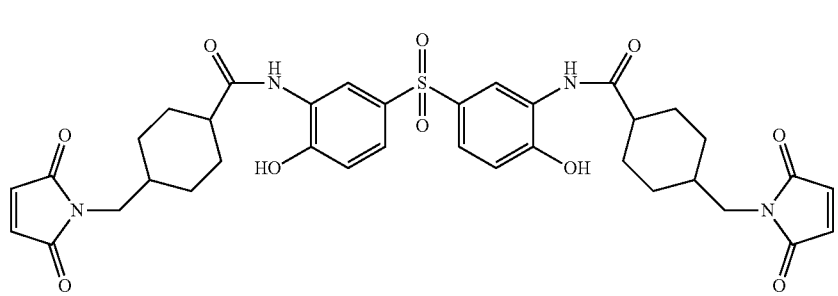

A-7

Example 8

Synthesis of Compound (Compound A-8) Represented by General Formula (1)

In a 500 ml round bottom flask equipped with a stirring bar coated with Teflon®, 19.3905 g (0.0918 mol) of 6-maleimidohexanoic acid (compound of No. 2 above) and 44.6085 g of NMP were charged. The mixture was cooled with ice. Thereafter, 12.5655 g (0.1056 mol) of thionyl chloride was slowly added thereto, and the mixture was stirred at 5° C. or lower for 30 minutes. Thereafter, a solution obtained by dissolving 8.5776 g (0.0306 mol) of bis (3-amino-4-hydroxyphenyl) sulfone (compound of No. 8 above), 0.019 g of BHT, 10.4572 g of NMP, and 7.1202 g of picoline was added thereto, and the mixture was stirred for 50 minutes. After 50 minutes, the whole amount of the solution was slowly added dropwise to 1000 g of water to obtain a solid of a target product. The solid was dissolved in 80 g of acetone, and the whole amount of the solution was slowly added dropwise to 1000 g of water to cause reprecipitation. The solid was dried under vacuum and collected. The amount of the obtained solid (compound A-8) was 20.40 g, and an yield thereof was 76%.

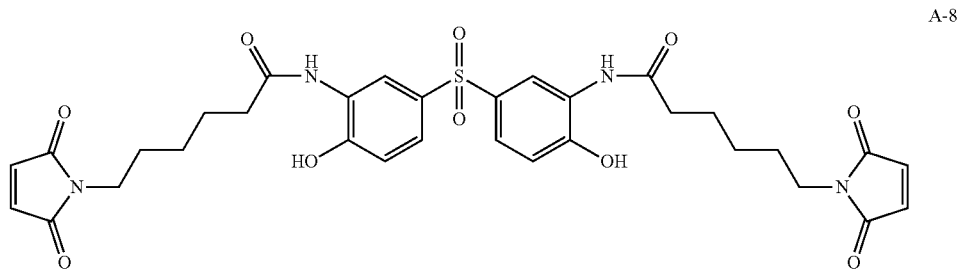 [SMILES: O=C(CCCCCN1C(=O)C=CC1=O)Nc1cc(S(=O)(=O)c2ccc(O)c(NC(=O)CCCCCN3C(=O)C=CC3=O)c2)ccc1O]

A-8

Example 9

Evaluation of Intramolecular (Dehydration) Ring-Closing Temperature of Compound of Present Invention For each of compounds (A-1) to (A-8) obtained in Examples 1 to 8, an intramolecular (dehydration) ring-closing temperature was measured under conditions at a temperature rising rate of 10° C./min in nitrogen using a differential thermogravimeter (TG/DTA 6200 manufactured by Seiko Instruments Inc.). The intramolecular (dehydration) ring-closing temperature of each of compounds (A-1) to (A-8) was lower than 300° C.

Examples 10 to 17

Preparation of Composition of Present Invention

Components were blended in the parts presented in Table 1 to prepare the composition of the present invention.

Comparative Example 1 (Preparation of Composition of Comparative Example 1)

Components were blended in the parts presented in Table 1 to prepare a comparative composition.
Bismaleimide compound C-1 was synthesized by a known method using the method described in U.S. Pat. No. 5,973,166 A.

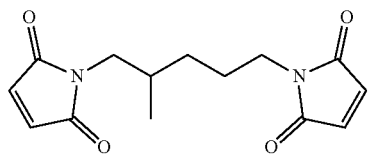

C-1

The components used in the compositions of Examples 10 to 17 and Comparative Example 1 presented in Table 1 are as follows.
A-1 to A-8: bismaleimide compounds A-1 to A-8 obtained in Examples 1 to 8
C-1: bismaleimide compound C-1
Photopolymerization initiator 2-1: 1-[9-ethyl-6-(2-methylbenzoyl)-9H-carbazol-3-yl] ethanone 1-(O-acetyloxime) ("IRGACURE OXE-02" manufactured by BASF Japan Ltd.)
Photopolymerization initiator 2-2: 2,4-diethylthioxanthone ("DETX-S" manufactured by Nippon Kayaku Co., Ltd.)

Preparation of Polymer Film and Polybenzoxazole Film of Present Invention and Comparative Cured Film Using an applicator, the composition obtained in each of Examples 10 to 17 was applied onto a 18 μm-thick copper foil, and then dried at 100° C. for 120 minutes to form a 20 μm-thick composition layer on the copper foil. The composition layer obtained above on the copper foil was exposed to light using a conveyor UV irradiation device CS 30L-1-1 manufactured by GS Yuasa Co., Ltd. such that an exposure amount at a wavelength of 365 nm was 1000 mJ/cm$^2$, and then heated at 150° C. for 60 minutes to obtain a film in which the polymer of the present invention was cured on the copper foil. Thereafter, the polymer film was heated at 300° C. for 60 minutes to undergo a ring-closing reaction, thereby obtaining the polybenzoxazole film of the present invention on the copper foil. Thereafter, the copper foil was removed by etching to obtain the polybenzoxazole film of the present invention separated from the copper foil.

In addition, using the composition obtained in Comparative Example 1, a comparative cured film separated from a copper foil was obtained by a method similar to the above.

Dielectric Properties of Polybenzoxazole Film and Comparative Cured Film: Evaluation of Dielectric Constant Dk and Dielectric Loss Tangent Df A plurality of pieces obtained by cutting each of the polybenzoxazole films obtained above into a length of 60 mm and a width of 3 mm were laminated on each other to prepare a polybenzoxazole film test piece having a film thickness of 50 to 300 μm. The obtained polybenzoxazole film test piece was dried in a desiccator filled with silica gel for 12 hours. A dielectric constant Dk and a dielectric loss tangent Df were measured as dielectric properties by a cavity resonator perturbation method using a vector type network analyzer ADMSO 10c1 manufactured by AET as a measuring instrument and using CP 531 (10 GHz band resonator) manufactured by KANTO Electronic Application and Development Inc. as a cavity resonator. As measurement conditions, a frequency was set to 10 GHz, and a measurement temperature was set to 25° C. Similarly, the dielectric properties of the comparative cured film were also measured. Results thereof are presented in Table 1.

Evaluation of 5% Weight Loss Temperature of Polybenzoxazole Film and Comparative Cured Film A weight loss temperature of each of the polybenzoxazole films prepared according to the "Preparation of polybenzoxazole film of present invention" was measured under a temperature rising condition of 10° C./min in nitrogen using a thermogravimetry-differential thermal analyzer (TG/DTA 6200 manufactured by Seiko Instruments Inc.) to determine a 5% weight loss temperature. Similarly, a 5% weight loss temperature of the comparative cured film was also measured. Results thereof are presented in Table 1.

Evaluation of Glass Transition Temperatures (Tg) of Polybenzoxazole Film and Comparative Cured Film A dynamic viscoelasticity of each of the polybenzoxazole films prepared according to the "Preparation of polybenzoxazole film of present invention" was measured using a dynamic viscoelasticity measuring device (DMA) (RSA-G2 manufactured by TA Instruments) under conditions of a frequency of 1 Hz, tensile mode, and a temperature rising rate of 3° C./min; and a glass transition temperature was determined from a maximum value of a loss tangent (tan δ). Similarly, the glass transition temperature of the comparative cured film was also measured. Results thereof are presented in Table 1.

Evaluation of Alkali Solubility of Composition

The composition obtained in each of Examples 10 to 17 and Comparative Example 1 was applied to a silicon substrate using a spin coater, and then dried at 95° C. for 15 minutes to form a 10 μm-thick composition layer on the silicon substrate. The obtained composition layer on the silicon substrate was immersed in 100 g of a 2.38% tetramethylammonium hydroxide aqueous solution (Tokusoh SD-1 manufactured by Tokuyama Corporation) for five minutes, and solubility was confirmed. Solubility was evaluated according to three criteria of good: o, medium: Δ, and poor: x.

TABLE 1

| Component | Material | Examples | | | | |
|---|---|---|---|---|---|---|
| | | BMI-F-2 1 | BMI-F-5 2 | BMI-F-C6 3 | BMI-B-5 4 | BMI-B-C6 5 |
| Bismaleimide compound | A-1 | 100 | | | | |
| | A-2 | | 100 | | | |
| | A-3 | | | 100 | | |
| | A-4 | | | | 100 | |
| | A-5 | | | | | 100 |
| | A-6 | | | | | |
| | A-7 | | | | | |
| | A-8 | | | | | |
| | C-1 | | | | | |
| Photopolymerization initiator | 2-1 | 5 | 5 | 5 | 5 | 5 |
| | 2-2 | 0.2 | 0.2 | 0.2 | 0.2 | 0.2 |
| Solvent | Cyclopentanone | 60 | 60 | 60 | | |
| | N-methyl-2-pyrrolidone | | | | 60 | 60 |
| Ring-closing temperature | | <300° C. | <300° C. | <300° C. | <300° C. | <300° C. |
| Dielectric properties | Dk | 2.4 | 2.2 | 2.5 | 2.9 | 2.9 |
| | Df | 0.0040 | 0.0054 | 0.0042 | 0.0076 | 0.0080 |
| Thermal properties | 5% Weight loss temperature | 300° C.< | 300° C.< | 300° C.< | 300° C.< | 300° C.< |
| | Tg | 300° C.< | 300° C.< | 300° C.< | 300° C.< | 300° C.< |
| Developability | Alkali solubility | o | o | o | o | Δ |

| Component | Material | Examples | | | Comp. Example |
|---|---|---|---|---|---|
| | | BMI-A-5 6 | BMI-S-C6 7 | BMI-S-5 8 | C-1 1 |
| Bismaleimide compound | A-1 | | | | |
| | A-2 | | | | |
| | A-3 | | | | |
| | A-4 | | | | |
| | A-5 | | | | |
| | A-6 | 100 | | | |
| | A-7 | | 100 | | |
| | A-8 | | | 100 | |
| | C-1 | | | | 100 |
| Photopolymerization initiator | 2-1 | 5 | 5 | 5 | 5 |
| | 2-2 | 0.2 | 0.2 | 0.2 | 0.2 |
| Solvent | Cyclopentanone | 60 | 60 | 60 | 60 |
| | N-methyl-2-pyrrolidone | | | | |
| Ring-closing temperature | | <300° C. | <300° C. | 300° C. | — |
| Dielectric properties | Dk | 2.6 | 2.6 | 2.7 | 2.7 |
| | Df | 0.0044 | 0.0059 | 0.0062 | 0.0021 |
| Thermal properties | 5% Weight loss temperature | 300° C.< | 300° C.< | 300° C.< | 300° C.< |
| | Tg | 300° C.< | 300° C.< | 200° C.< | 284° C. |
| Developability | Alkali solubility | o | o | o | x |

The polymer having the structural unit of the present invention represented by formula (2) is a photosensitive polybenzoxazole precursor having negative pattern-forming ability, and makes it possible to use an alkaline aqueous solution for pattern formation. Therefore, it is possible to completely eliminate industrial waste of an organic solvent which has been generated in a large amount so far. In addition, since the polybenzoxazole film finally obtained has excellent heat resistance and electrical properties, the polybenzoxazole film can be used as a surface protective film of a semiconductor that is usually used, an interlayer insulating film thereof, and an insulating film of a rewiring layer thereof. The present invention relates to a resin backbone itself used in a photosensitive resin composition and a method for manufacturing the resin backbone. These are based on totally novel inventions, and those skilled in the art can easily appreciate that these are unique and significantly excellent inventions.

Other modifications and variations will be apparent to those skilled in the art in view of the above detailed description of the invention. However, it is evident that such other modifications and variations can be performed without departing from the spirit and scope of the invention.

The invention claimed is:

1. A bismaleimide compound comprising, in one molecule, two partial structures in each of which a carbon atom having a substituent represented by the following formula (A):

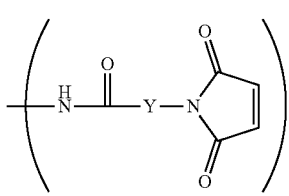
(A)

wherein Y represents a direct bond or a divalent linking group, and
a carbon atom having a hydroxy group are directly bonded to each other, wherein the bismaleimide compound is represented by the following formula (1):

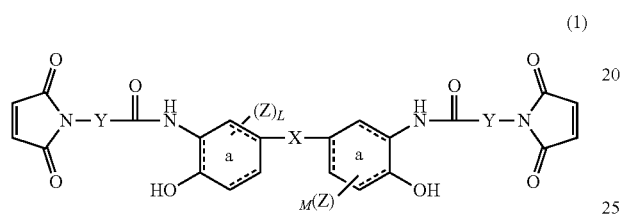
(1)

wherein ring a represents a benzene ring or a cyclohexane ring, X and Y each independently represent a direct bond or a divalent linking group, the plurality of Ys may be the same as or different from each other, Z represents a monovalent substituent bonded to ring a, when there is a plurality of Zs, Zs may be the same as or different from each other, and L and M each represent the number of substituents Zs and each independently represent an integer of 0 to 3.

2. The bismaleimide compound according to claim 1, wherein X represents a direct bond or a divalent linking group containing one or more selected from the group consisting of a carbon atom, a fluorine atom, a sulfur atom, and an oxygen atom.

3. The bismaleimide compound according to claim 2, wherein
X represents a direct bond or a divalent linking group represented by any one of the following formulas (a) to (f):

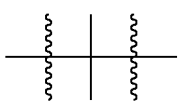
(a)

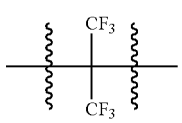
(b)

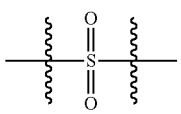
(c)

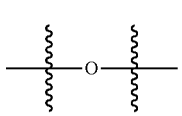
(d)

(e)

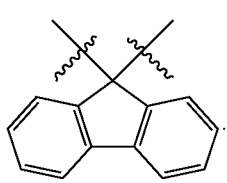
(f)

4. The bismaleimide compound according to claim 1, wherein Y represents an alkylene group having 1 to 11 carbon atoms or an alkylene group having 1 to 11 carbon atoms and including a divalent aromatic group.

5. A composition comprising the bismaleimide compound according to claim 1 and a compound capable of reacting with a maleimide group.

6. A composition comprising the bismaleimide compound according to claim 1 and a photopolymerization initiator or a curing catalyst.

* * * * *